(12) United States Patent
Murakami et al.

(10) Patent No.: US 8,323,566 B2
(45) Date of Patent: Dec. 4, 2012

(54) LIQUID SAMPLE ANALYSIS DEVICE

(75) Inventors: Kenji Murakami, Ehime (JP); Masahiro Aga, Ehime (JP); Hideyuki Kurokawa, Ehime (JP); Takahiko Tanida, Ehime (JP); Ryosuke Yamada, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/056,247

(22) PCT Filed: Jul. 28, 2009

(86) PCT No.: PCT/JP2009/003539
§ 371 (c)(1),
(2), (4) Date: Jan. 27, 2011

(87) PCT Pub. No.: WO2010/021088
PCT Pub. Date: Feb. 25, 2010

(65) Prior Publication Data
US 2011/0129909 A1    Jun. 2, 2011

(30) Foreign Application Priority Data

Aug. 22, 2008  (JP) ................................ 2008-213410

(51) Int. Cl.
*G01N 1/10* (2006.01)
*G01N 33/52* (2006.01)

(52) U.S. Cl. .......... 422/64; 422/400; 422/402; 422/404; 422/63; 422/68.1; 356/244; 356/246; 436/46; 436/164

(58) Field of Classification Search .................. None
See application file for complete search history.

(56) References Cited

U.S. PATENT DOCUMENTS

| 4,412,742 | A | * | 11/1983 | Lloyd ............................. 356/73 |
| 2003/0205097 | A1 | | 11/2003 | Wickstead et al. |
| 2008/0083619 | A1 | | 4/2008 | Takahashi et al. |
| 2008/0257020 | A1 | * | 10/2008 | Jung et al. .................... 73/64.56 |
| 2011/0053291 | A1 | * | 3/2011 | Matsuda et al. .............. 436/514 |

FOREIGN PATENT DOCUMENTS

| EP | 2251691 | | 11/2010 |
| JP | 11-051937 | | 2/1999 |
| JP | 3655283 | | 3/2005 |
| JP | 2005-515431 | | 5/2005 |
| JP | 2008-006343 | | 1/2008 |
| JP | 2008-170187 | | 7/2008 |
| WO | WO-2006/034104 | * | 3/2006 |
| WO | WO2007/065695 | | 6/2007 |
| WO | 2009-090861 | | 7/2009 |

* cited by examiner

*Primary Examiner* — P. Kathryn Wright
(74) *Attorney, Agent, or Firm* — Hamre, Schumann, Mueller & Larson, P.C.

(57) ABSTRACT

A liquid sample analysis device includes a holder part 11 holding a test piece 1, an optical system 20 that optically detects a reaction state of a liquid sample and a reagent, and a support member 30 that integrally supports the holder part 11 and the optical system 20. The orientation of the test piece 1 is changed with respect to the direction of gravitational force by rotating the support member 30.

4 Claims, 4 Drawing Sheets

FIG. 4A
PRIOR ART
FIG. 4B
PRIOR ART
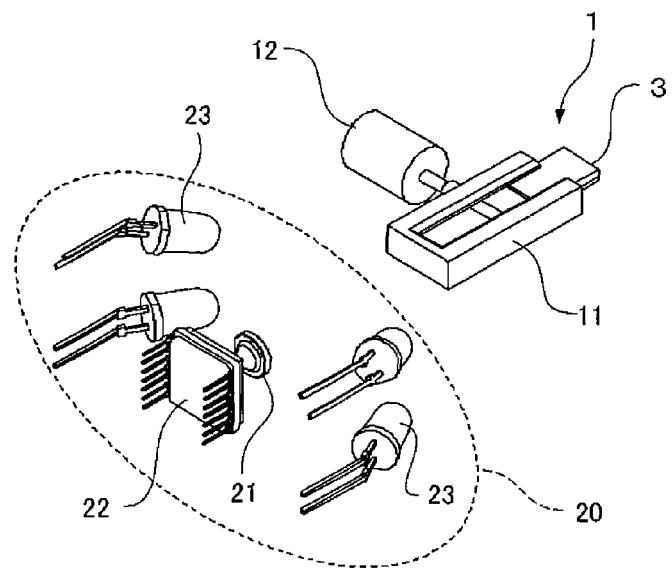
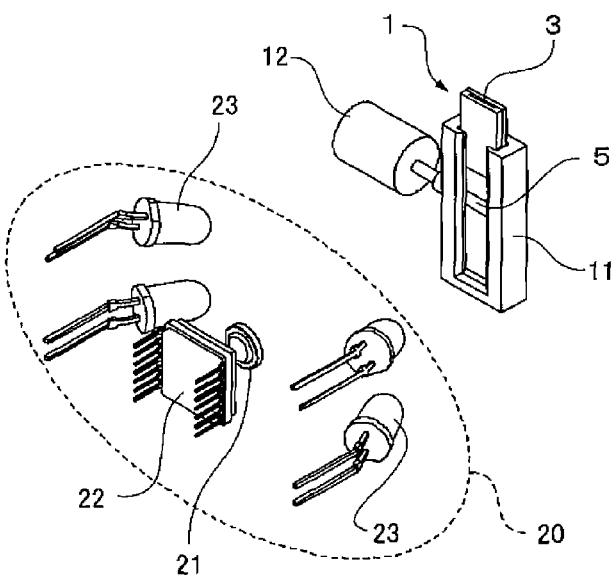

LIQUID SAMPLE ANALYSIS DEVICE

TECHNICAL FIELD

The present invention relates to a liquid sample analysis device in which a liquid sample is added to a test piece, the liquid sample is developed in the test piece by capillarity, and a reaction state of a reagent retained on the test piece and the liquid sample is optically detected to analyze a component in the liquid sample. To be specific, the present invention relates to a liquid sample analysis device that stabilizes the developing speed of a liquid sample or a mixed state of the liquid sample and a reagent by changing the orientation of a test piece with respect to the direction of gravitational force after the sample is added.

BACKGROUND ART

Liquid sample analysis devices using an immunochromatographic method have been widely used for analyzing liquid samples such as blood of living bodies. FIG. 2 shows an example of a test piece for analysis using the immunochromatographic method. FIG. 2(a) is a plan view (top view) and FIG. 2(b) is a sectional view. In a test piece 1, a sample adding portion 3 and a sample developing layer 4 are formed on a substrate 2. A liquid sample such as blood is added to the sample adding portion 3 by dropping or the like and the added liquid sample is developed in the sample developing layer 4. Further, an antibody reagent 5 is retained at the center of the sample developing layer 4 in the longitudinal direction or on the downstream side of the test piece 1 (hereinafter, a side where the sample adding portion 3 is provided on a longitudinal end of the test piece 1 will be called the upstream side and the other side will be called the downstream side), and a dye labeling reagent 6 that binds to a specific antigen to be measured in the liquid sample is retained upstream of the sample developing layer 4. The sample adding portion 3 is formed by a clearance between the substrate 2 and a cover member 7. The sample developing layer 4 is composed of a nonwoven fabric or a porous material. On the surface of the sample developing layer 4, a protective member such as a transparent sheet (not shown) may be bonded to prevent drying of the liquid sample during the development of the sample.

In analysis, the liquid sample (not shown) added to the sample adding portion 3 of the test piece 1 fills the sample adding portion 3 and then reaches the upstream end of the sample developing layer 4 provided downstream of the sample adding portion 3. The liquid sample at the sample developing layer 4 dissolves the dye labeling reagent 6 retained upstream of the sample developing layer 4 and the dye labeling reagent 6 binds to the specific antigen in the liquid sample. The liquid sample having reacted with the dye labeling reagent 6 further flows downstream through the sample developing layer 4 by capillarity and reaches the antibody reagent 5, so that the antibody reagent 5 captures the specific antigen in the liquid sample by an antigen-antibody reaction. The dye labeling reagent 6 has bound to the captured antigen and thus coloration occurs in a region where the antibody reagent 5 is retained on the sample developing layer 4, according to the concentration of the specific antigen in the liquid sample.

The concentration of the specific antigen in the liquid sample can be measured by optically detecting the coloration. Optical detection methods include a method of irradiating the test piece 1 with laser light and detecting scattered light from the test piece 1 with a photodiode, and a method of imaging the test piece 1 with an image sensor and determining absorbance by image processing on the obtained image. Various liquid sample analysis devices have been proposed using these methods.

In the case where blood is used as a liquid sample without undergoing pretreatment such as cytapheresis, the blood contains solid matters, e.g., blood cell components such as red blood cells and thus the liquid sample (blood) flowing as it is through the sample developing layer 4 may cause the blood cell components to clog at the fibers of the nonwoven fabric or the holes of the porous material, so that the liquid sample may not be normally developed. In order to minimize the occurrence of such a problem, a method has been used in which the sample adding portion 3 contains a blood cell constrictor 8. In this method, the blood cell components in the liquid sample (blood) added by dropping or the like are constricted and then the liquid sample is passed through the sample developing layer 4 (e.g., patent document 1).

In FIG. 3(a), the liquid sample added to the sample adding portion 3 is analyzed while the test piece 1 is held in horizontal position. In this case, the velocity of the liquid sample traveling in the sample developing layer 4 varies depending on the viscosity of the liquid sample, causing variations in the quantity of a liquid sample passing through, in a predetermined time, the retaining portion of the antibody reagent 5 on the sample developing layer 4. Thus an error occurs in analysis results. Moreover, when the liquid sample has an extremely high viscosity, the liquid sample may not reach, within the predetermined time, the retaining portion of the antibody reagent 5 on the sample developing layer 4.

In FIG. 3(b), the liquid sample added to the sample adding portion 3 is analyzed while the test piece 1 is held in vertical position such that the upstream side of the sample developing layer 4 is placed upward along the vertical direction. In this case, the liquid sample added to the sample adding portion 3 flows into the sample developing layer 4 by a gravitational force before the blood cell constrictor 8 retained in the sample adding portion 3 sufficiently dissolves. Thus the liquid sample may not be normally developed to the downstream side of the sample developing layer 4.

To address this problem, the inventors of the present invention have devised a liquid sample analysis device that stabilizes the developing velocity of a liquid sample and a mixed state of the liquid sample and a reagent by changing the orientation of the test piece 1 with respect to the direction of gravitational force after the sample is added.

FIG. 4 shows an example of the configuration of the devised liquid sample analysis device according to the related art. FIG. 4(a) is a perspective view showing a state at the addition of the liquid sample. FIG. 4(b) is a perspective view showing a state at the development of the sample.

In FIG. 4, reference numeral 1 denotes the test piece, reference numeral 11 denotes a holder part that holds the test piece 1, reference numeral 12 denotes a motor (rotating device) for rotating the holder part 11, and reference numeral 20 denotes an optical system for imaging the colored portion (the retaining portion of the antibody reagent 5) of the test piece 1. In the optical system 20, reference numeral 21 denotes a lens, reference numeral 22 denotes an image sensor, and reference numeral 23 denotes a light source that illuminates the surface of the test piece 1. The optical system 20 forms an image of the colored portion (the antibody reagent 5) of the test piece 1 on the imaging surface of the image sensor 22 through the lens 21.

In analysis, as shown in FIG. 4(a), the test piece 1 is first held in horizontal position and the liquid sample (blood) is added (dropped) to the sample adding portion 3. The sample adding portion 3 contains the blood cell constrictor 8 that is dissolved by the added liquid sample and is mixed with the liquid sample, so that blood cell components in the liquid sample (blood) are constricted. When blood cells are constricted after a lapse of a predetermined time, the motor 12 rotates the holder part 11 such that the upstream side of the test piece 1 is placed upward along the vertical direction as shown in FIG. 4(b). Thus the liquid sample containing the blood cells having been sufficiently constricted by the blood cell constrictor 8 flows toward the downstream side of the sample developing layer 4. In this case, the liquid sample simultaneously receives a capillary force generated by the sample developing layer 4 and a gravitational force applied to the downstream side of the sample developing layer 4, thereby stabilizing the developing speed of the liquid sample. Even when the liquid sample has a high viscosity, the liquid sample can develop to the retaining portion of the antibody reagent 5 within the predetermined time.

Citation List

Patent Literature

Patent Literature 1: Japanese Patent No. 3655283

SUMMARY OF INVENTION

Technical Problem

In the liquid sample analysis device configured according to the related art, the holder part 11 holding the test piece 1 is rotated by the motor 12 to change the orientation of the test piece 1. Thus when the holder part 11 is rotated, the relative positions of the test piece 1 and the optical system 20 are changed disadvantageously.

Thus each time the test piece 1 is imaged after the sample is developed, it is necessary to control the test piece 1 in the same position. Because of variations in the stop position of the motor 12 and rattling of a bearing (not shown) that rotationally supports the holder part 11, the relative positions of the test piece 1 and the optical system 20 typically slightly change each time, resulting in an error in measurement results and incorrect analysis.

Particularly, in order to eliminate the influence of a state of the test piece 1, e.g., roughness and uneven illumination on the test piece 1, the test piece 1 may be imaged before the addition of the liquid sample, and an image captured after the development of the sample may be corrected based on the previous image. In such a liquid sample analysis device, when the relative positions of the test piece 1 and the optical system 20 are shifted from each other, misalignment occurs between the previous image and the image captured after the development of the sample, resulting in insufficient correction and an error in measurement results.

The present invention has been devised to solve the problems of the related art. An object of the present invention is to provide a liquid sample analysis device that can conduct correct analysis without changing the relative positions of a test piece and an optical system even when the orientation of the test piece is changed with respect to the direction of gravitational force.

Solution to Problem

In order to solve the problems of the related art, the present invention is a liquid sample analysis device in which a liquid sample is added to a test piece, the liquid sample is developed in the test piece by capillarity, and a reaction state of a reagent retained on the test piece and the liquid sample is optically detected to analyze a component in the liquid sample, the liquid sample analysis device including: a holder part holding the test piece; an optical system that optically detects the reaction state of the liquid sample and the reagent; a support member integrally supporting the holder part and the optical system; and a rotating device that rotates the support member, wherein the support member is rotated to change the orientations of the test piece and the optical system with respect to the direction of gravitational force.

With this configuration, the support member integrally supports the holder part holding the test piece and the optical system that optically detects the reaction state of the test piece, and the overall support member is rotated. Thus even when the test piece is rotated, the relative positions of the test piece and the optical system do not change.

The liquid sample analysis device of the present invention further includes a control unit that allows the test piece to be supported in horizontal position when the liquid sample is added, and changes the orientation of the test piece such that the sample adding portion of the test piece is placed on the top of the test piece after a lapse of a predetermined time since the addition of the liquid sample.

The liquid sample analysis device of the present invention further includes a control unit that records data of a state of the test piece before the liquid sample is added, and corrects a state of the test piece after the liquid sample is developed, based on the recorded data.

The liquid sample analysis device of the present invention further includes a sensor that detects the orientation of the main unit of the device with respect to the direction of gravitational force.

The liquid sample analysis device of the present invention further includes a warning device that warns an operator when the sensor detects that an error exceeds a predetermined angle between a normal orientation and the orientation of the main unit of the device with respect to the direction of gravitational force.

The liquid sample analysis device of the present invention, wherein the sensor is a gravitation sensor.

The liquid sample analysis device of the present invention, wherein the liquid sample is blood.

ADVANTAGEOUS EFFECTS OF INVENTION

According to the liquid sample analysis device of the present invention, a support member integrally supports a holder part holding a test piece and an optical system that optically detects a reaction state of the test piece, and the test piece and the optical system are integrally rotated. Thus even when the orientation of the test piece is changed with respect to the direction of gravitational force, the relative positions of the test piece and the optical system do not change, achieving precise analysis.

BRIEF DESCRIPTION OF THE DRAWINGS

FIG. 4(a) is a perspective view showing the configuration of a liquid sample analysis device in a state in which a sample is dropped (added) according to the related art.

FIG. 4(b) is a perspective view showing the configuration of the liquid sample analysis device in a state in which the sample is developed according to the related art.

DESCRIPTION OF EMBODIMENTS

Figure 1A:
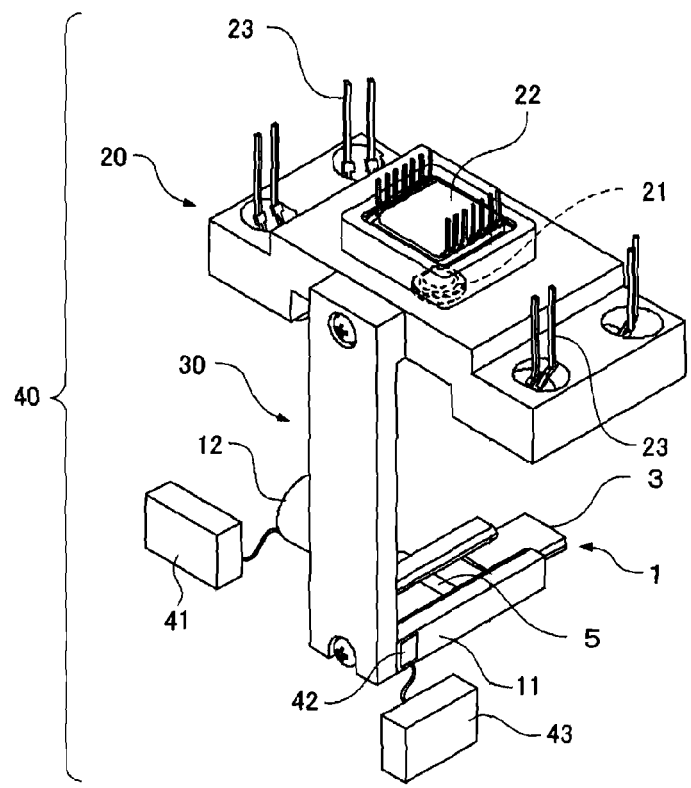
FIG. 1(a) is a perspective view showing the configuration of a liquid sample analysis device in a state in which a sample is dropped (added) according to an embodiment of the present invention.

A liquid sample analysis device according to an embodiment of the present invention will be specifically described below in accordance with the accompanying drawings. Constituent elements having the same functions as the liquid sample analysis device of the related art will be indicated by the same reference numerals and the explanation thereof is partially omitted.

Figure 1B:
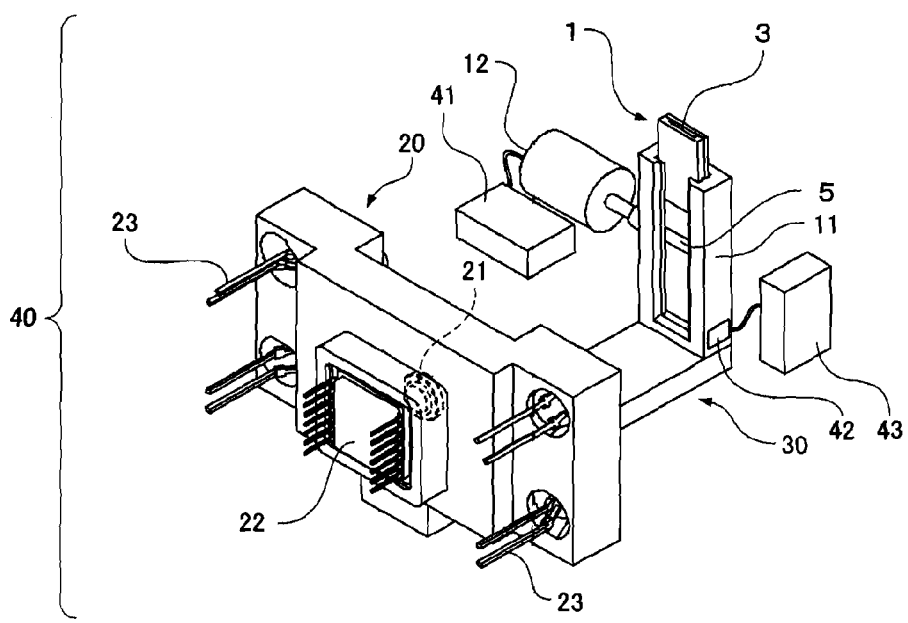
FIG. 1(b) is a perspective view showing the configuration of the liquid sample analysis device in a state in which the sample is developed according to the embodiment of the present invention.
Figure 2A:
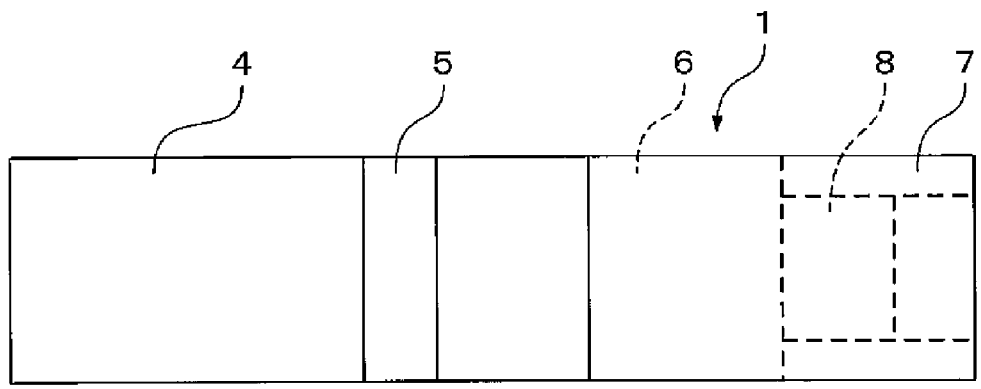
FIGS. 2(a) and 2(b) are a plan view (top view) and a sectional view showing an example of a test piece using an immunochromatographic method.
Figure 2B:
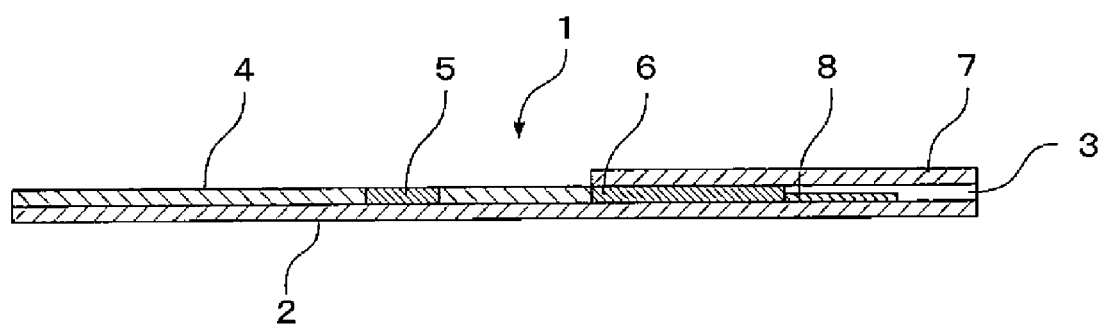
Figure 3A:
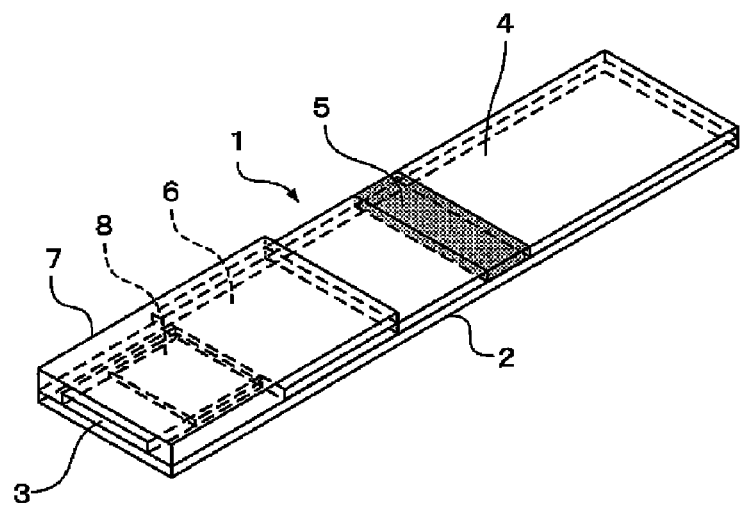
FIG. 3(a) is a perspective view showing a state of the test piece with the dropped sample (the added liquid sample).
Figure 3B:
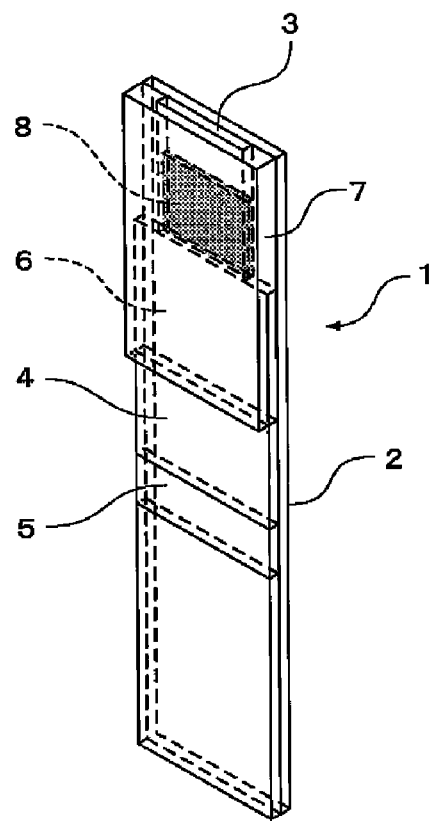
FIG. 3(b) is a perspective view showing a state of the test piece with the developed sample.

FIGS. 1(a) and 1(b) are perspective views showing the configuration of the liquid sample analysis device according to the embodiment of the present invention. FIG. 1(a) shows a state of the liquid sample analysis device with a dropped sample (an added liquid sample) and FIG. 1(b) shows a state of the liquid sample analysis device with the developed sample.

In FIG. 1, reference numeral 11 denotes a holder part holding a test piece 1 and reference numeral 20 denotes an optical system that optically detects a reaction state of the liquid sample and a reagent in the test piece 1. The holder part 11 and the optical system 20 are integrally supported by a support member 30 in a state in which an image sensor 22 provided in the optical system 20 is opposed to the test piece 1 held by the holder part 11. The liquid sample analysis device 40 includes the holder part 11 holding the test piece 1, the optical system 20 that optically detects a reaction state of the liquid sample and the reagent, the support member 30, a motor 12 acting as a rotating device for rotating the support member 30, and a control unit 41 that performs a controlling operation which will be described later. The orientation of the test piece 1 is changed with respect to the direction of gravitational force by rotating the holder part 11 that is integrally supported with the optical system 20 by the support member 30.

As shown in FIG. 1(a), first in analysis, the test piece 1 is held in horizontal position by the control unit 41. Then, the test piece 1 is imaged (preliminary imaging) by the image sensor 22 of the optical system 20 to record states such as roughness and uneven illumination on the test piece 1 before the sample is added (dropped). In this state, blood is added as a liquid sample to a sample adding portion 3.

After the addition of the liquid sample is detected (for example, the addition is detected by the image sensor 22 of the optical system 20), the liquid sample is mixed with a blood cell constrictor 8. After a lapse of a predetermined time for the constriction of blood cells in the liquid sample, the motor 12 rotates the holder part 11 and the optical system 20 that are integrally supported by the support member 30, so that as shown in FIG. 1(b), the test piece 1 is held in vertical position such that the sample adding portion 3 on one end of the test piece 1 is placed on the top of the test piece 1 along the vertical direction. Thus the liquid sample containing the blood cells sufficiently constricted by the blood cell constrictor 8 flows to the downstream side of a sample developing layer 4.

In this case, the liquid sample simultaneously receives a capillary force generated by the sample developing layer 4 and a gravitational force applied to the downstream side of the sample developing layer 4, thereby stabilizing the developing speed of the liquid sample. Even when the liquid sample has a high viscosity, the liquid sample can develop to the retaining portion of an antibody reagent 5 within a predetermined time. After the liquid sample is developed and the antibody reagent 5 is colored, the test piece 1 is imaged (main imaging) by the image sensor 22 of the optical system 20 and the image is corrected using the previous image. After that, the absorbance of the retaining portion of the antibody reagent 5 is determined by image processing and is converted to a concentration of a target analyte. Analysis is completed thus.

In the present embodiment shown in FIG. 1, the support member 30 is illustrated as a plate member to clarify the internal structure of the liquid sample analysis device. The support member 30 may be shaped like a box covering the optical system 20 and the holder part 11, in consideration of blocking of extraneous light during analysis and the strength of the liquid sample analysis device. Further, in the present embodiment shown in FIG. 1, the shaft of the motor 12 is connected to the holder part 11. The present invention is not limited to this configuration and the rotating shaft of the motor 12 may be connected to any one of the optical system 20, the holder part 11, and the support member 30 of an integral structure with the same effect. In order to reduce the size of the liquid sample analysis device by reducing the turning radius of the motor 12, the rotating shaft of the motor 12 is preferably located near the center of the integral structure made up of the optical system 20, the holder part 11, and the support member 30. Moreover, in the present embodiment shown in FIG. 1, the rotating shaft of the motor 12 is directly connected to the holder part 11. The present invention is not limited to this configuration and a reduction mechanism with a proper reduction ratio may be provided in consideration of the properties of the motor 12 and a time required for a change of orientation.

In the case where the main unit of the device is not placed in normal position where the developing direction of the test piece and the direction of gravitational force are aligned with each other, for example, in the case where the main unit of the device is set on a tilted base or is laid down, an error occurs in the orientations of the test piece and the optical system with respect to the direction of gravitational force even if the support member that supports the test piece and the optical system is rotated according to the steps, so that the accuracy of analysis decreases. If such a state is expected, a sensor 42 for detecting the orientation of the main unit with respect to the direction of gravitational force is provided in the main unit. When an error between the normal orientation and the orientation of the main unit exceeds a predetermined angle with respect to the direction of gravitational force, a warning device 43 provides warning display or an alarm sound to notify an operator that the main unit of the device should be returned to the normal orientation. Thus a decrease in the accuracy of analysis can be prevented. The sensor 42 for detecting the orientation of the main unit of the device with respect to the direction of gravitational force is preferably a gravitation sensor (acceleration sensor) that is inexpensive, precise, and small in size suitably for the liquid sample analysis device of the present invention.

As has been discussed, in the liquid sample analysis device of the present embodiment, the holder part 11 and the optical system 20 are integrally supported by the support member 30. Thus the relative positions of the test piece 1 and the optical system 20 do not vary between the preliminary imaging and the main imaging, and an image is precisely corrected in the main imaging by using a preliminary image, achieving high accuracy of analysis.

Industrial Applicability

The liquid sample analysis device of the present invention is particularly suitable for a liquid sample analysis device that requires sensitive analysis and can conduct precise analysis without changing the relative positions of a test piece and an optical system even when the orientation of the test piece is changed with respect to the direction of gravitational force.

The invention claimed is:

1. A liquid sample analysis device in which a liquid sample is added to a test piece, the liquid sample is developed in the test piece by capillarity, and a reaction state of a reagent retained on the test piece and the liquid sample is optically detected to analyze a component in the liquid sample, the liquid sample analysis device comprising:
the test piece comprising a substrate having a sample adding portion on one side of the test piece and a developing layer that extends to another side of the substrate;
a holder part holding the test piece;
an optical system that optically detects the reaction state of the liquid sample and the reagent;
a support member integrally supporting the holder part and the optical system;
a rotating device that rotates the support member;
a control unit that controls the rotating device to allow the test piece to be supported in a horizontal position when the liquid sample is added to the sample adding portion, and changes the orientation of the test piece such that the sample adding portion of the test piece is supported in a vertical position for detection of the reaction state of the liquid sample and reagent by the optical system after a lapse of a predetermined time since the addition of the liquid sample; and
a sensor that detects the orientation of the test piece with respect to the direction of gravitational force;
wherein the support member is rotated to change orientations of the test piece and the optical system with respect to a direction of gravitational force.

2. The liquid sample analysis device according to claim 1, wherein the control unit records data of a state of the test piece before the liquid sample is added, and corrects a state of the test piece after the liquid sample is developed, based on the recorded data.

3. The liquid sample analysis device according to claim 1, further comprising a warning device that warns an operator when the sensor detects that an error exceeds a predetermined angle between a normal orientation and the orientation of the test piece with respect to the direction of gravitational force.

4. The liquid sample analysis device according to claim 1, wherein the sensor is a gravitation sensor.

* * * * *